United States Patent [19]
Langhorst

[11] Patent Number: 4,818,264
[45] Date of Patent: Apr. 4, 1989

[54] MULTICAPILLARY GAS CHROMATOGRAPHY COLUMN

[75] Inventor: Marsha L. Langhorst, Midland, Mich.

[73] Assignee: The Dow Chemical Company, Midland, Mich.

[21] Appl. No.: 44,396

[22] Filed: Apr. 30, 1987

[51] Int. Cl.[4] .................. C03B 23/20; B01D 15/08
[52] U.S. Cl. ................................ 65/4.3; 55/386; 65/3.4
[58] Field of Search ............... 55/67, 197, 386; 73/23.1; 210/198.2; 65/3.4, 4.1, 4.3, 3.43, 3.44

[56] References Cited

U.S. PATENT DOCUMENTS

| | | | |
|---|---|---|---|
| 3,949,806 | 4/1976 | Dunges | 55/67 X |
| 4,350,586 | 9/1982 | Conlon et al. | 55/197 X |
| 4,424,127 | 1/1984 | Roeraade | 55/386 X |
| 4,451,365 | 5/1984 | Sättler et al. | 55/386 X |
| 4,657,742 | 4/1987 | Beaver | 55/386 X |

FOREIGN PATENT DOCUMENTS 61-265567 11/1986 Japan .

OTHER PUBLICATIONS

Aleksander Janik, "Multicapillary Columns", J. of Chromatographic Science, vol. 14, 12/76, 589.
H. D. Pierce, Jr. et al., "Technical Note: A Method for the Preparation of Glass Multicapillary Columns", vol. 17, J. of Chromatographic Science, 5/79, 297.
Walter Jennings, "Gas Chromatography with Glass Capillary Columns, 2 Ed.", Academic Press, 1980, 34-35.

*Primary Examiner*—Robert Spitzer
*Attorney, Agent, or Firm*—Timothy S. Stevens

[57] ABSTRACT

A multicapillary gas chromatography column comprising a bundle of single capillary columns each of which have essentially the same internal diameter and which are coated with essentially the same thickness of essentially the same stationary phase so that each column has essentially the same standard retention factor. A method of producing such a column is to cut a single fused silica capillary column into a number of essentially equal lengths and then to bundle the lengths together. Each bundle end can then be inserted into, for example, a graphite ferrule and then the multicapillary column can be conventionally installed into a gas chromatograph. The multicapillary column of the invention has the injection, detection and sample capacity advantages of a relatively large diameter capillary column with the speed and resolving power of a relatively narrow diameter capillary column.

2 Claims, 1 Drawing Sheet

MULTICAPILLARY GAS CHROMATOGRAPHY COLUMN

FIELD OF THE INVENTION

The invention is in the field of gas chromatography and more specifically in the field of capillary gas chromatography.

BACKGROUND OF THE INVENTION

Capillary column gas chromatography (CC-GC) is an important branch of chemical analysis because of the excellent resolving power and speed of analysis of CC-GC One of the primary characteristics of the columns used in CC-GC is the internal diameter of the column. The use of a relatively small internal diameter column, e.g., 0.1 millimeter, can result in much better resolving power and speed of analysis than the use of a relatively large internal diameter column, e.g., 0.5 millimeter. Nevertheless, the use of relatively large internal diameter columns is increasing because of practical considerations. For example, problems of injection and detection are less complicated with the use of relatively large internal diameter columns. Relatively Large internal diameter columns with thick films are also chosen for applications requiring high capacity or large injections to detect trace components of the sample. However, the high capacity and sensitivity is achieved while compromising speed and separating efficiency, i.e., usually chromatographers must balance or choose between speed of analysis, efficiency and capacity.

It would be desirable to have a column for CC-GC that had the practical advantages of a relatively large internal diameter column and the resolving power, capacity and speed of analysis of the relatively small internal diameter columns.

A multicapillary column for CC-GC comprising thousands of individual columns for capillary preparative chromatography was suggested and then dismissed by Dr. M. J. E. Golay (the inventor of CC-GC) during the opening address at the First International Symposium on Glass Capillary Chromatography in 1975 as reported by Aleksander Janik in the December 1976 issue of Journal of Chromatographic Science on page 589. Golay stated "The second is capillary preparative chromatography. Here, perhaps we make a brief bow to that most theoretical possibility, and go on. Indeed, who would like to manifold a thousand capillaries, all painfully trimmed to the same retention time for a given substance and a given pressure drop, and trust that their properties have been stabilized forever. It is too fantastic."

Despite Golay's negative comments, Janik proceeded to suggest two designs for multicapillary columns. The first was a bundle of wires with the capillary space being between the wires. The second was an assemblage of profiled plates with the capillary space being between the plates.

H. D. Pierce, Jr., et al evaluated the designs of Janik and concluded in an article published in Journal of Chromatographic Science, May 1979, page 297, that the designs of Janik were faulted, e.g., because the capillary spaces were not of circular cross section. Pierce, Jr. et al designed an improved system having seven single glass capillary columns, of about 0.2 millimeter internal diameter each, closely bundled inside a glass tube casing. Pierce, Jr. et al made their multicapillary column by placing seven 1.8 millimeter outside diameter by 1.4 millimeter inside diameter glass tubes inside an 8 millimeter outside diameter by 6 millimeter inside diameter glass tube and then drawing this assembly with a glass tube drawing machine.

Walter Jennings evaluated the design of Pierce, Jr. et al in the book Gas Chromatography with Glass Capillary Columns, Second Edition, 1980, Academic Press, New York, pages 34 and 35, and stated "At our present state of the art, however, it is doubtful whether the phase ratios would be identical in each flow path. This would result in each solute exhibiting a range of partition ratios, resulting in broadened peaks." In the present disclosure a multicapillary column having different phase ratios between at least two of the individual capillaries of the same length, for example, is termed an "unbalanced multicapillary gas chromatography column" and the chromatogram resulting from the use of such an unbalanced column is termed an "unbalanced chromatogram." The above referred to publications are herein fully incorporated by reference.

The state of the art of CC-GC was significantly advanced by the development of fused silica capillary gas chromatography columns in 1979. The fused silica columns are drawn at high temperature, e.g. 2,000° C., using advanced fiber optics technology. The fused silica column is generally also given a polymeric outer coating to increase the break resistance of the column with a polyamide coating being the most popular. The fused silica column is then processed to coat a chromatographically active stationary phase on the inside of the capillary. Fused silica capillary gas chromatography columns are widely available commercially from, for example, J&W Instruments Inc., New Brighton MN.

SUMMARY OF THE INVENTION

One embodiment of the invention is a balanced multicapillary gas chromatography column that comprises a plurality of single capillary gas chromatography columns, each of which is essentially the same type and each of which has essentially the same standard retention factor. The capillary columns that comprise the invention are all the same length. The capillary columns that comprise the invention are all cut from one original capillary column. The plurality of single capillary gas chromatography columns can be a plurality of fused silica capillary gas chromatography columns.

Another embodiment of the invention is a method of making a balanced multicapillary gas chromatography column by a method that comprises two steps. The first step is to cut a single capillary gas chromatography column into a plurality of essentially equal length sections. The second step is to bundle the sections together in parallel. Each bundle end can then be inserted into, for example, a graphite ferrule and then conventionally installed into a gas chromatograph. The column from which the sections are cut can be a fused silica capillary gas chromatography column.

DETAILED DESCRIPTION OF THE INVENTION

Figure 1:
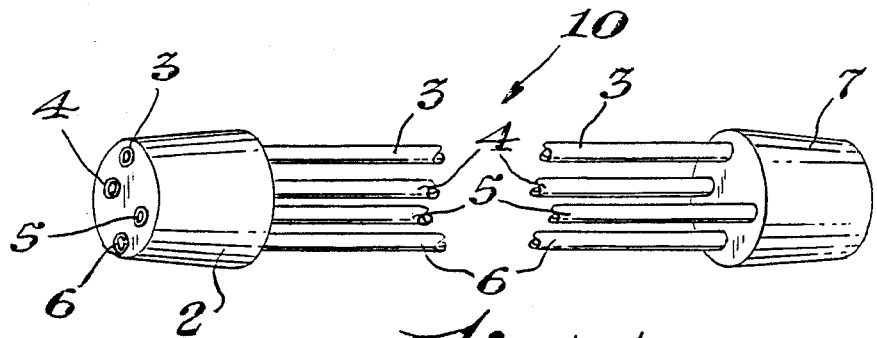
FIG. 1 is an isometric view of a typical balanced multicapillary gas chromatography column of the invention, the individual capillaries of which are shown foreshortened.

Referring to FIG. 1, therein is shown a foreshortened typical balanced multicapillary gas chromatography column 10 of the present invention including a first multi-holed ferrule 2. The ferrule 2 defines four bores therethrough. Inserted into one of the bores of the ferrule 2 is one end of a fused silica gas chromatography column 3. Inserted into another of the bores of the ferrule 2 is one end of a fused silica gas chromatography column 4. Inserted into yet another of the bores of the ferrule 2 is one end of a fused silica gas chromatography column 5. Inserted into the remaining bore of the ferrule 2 is one end of a fused silica gas chromatography column 6. Inserted into one of the bores of a second multi-holed ferrule 7 is the other end of the column 3. Inserted into another bore of the ferrule 7 is the other end of the column 4. Inserted into yet another of the bores of the ferrule 7 is the other end of the column 5. Inserted into the remaining bore of the ferrule 7 is the other end of the column 6. Preferably the ferrules 2 and 7 are graphite ferrules. Multi-holed ferrules can be made by drilling a solid ferrule (available from J&W Instruments, supra) with a wire drill and pin vice. The diameter of the wire drill should be slightly larger than the outside diameter of the individual columns. The multicapillary column 10 can be mounted in a gas chromatograph in the conventional manner by positioning a tubing nut, not shown, behind each of the ferrules 2 and 7 and then tightening each nut so that a leak tight connection is made, as is well understood in the art. The columns 3, 4, 5, and 6 are all the same length. It is critical that the columns 3, 4, 5, and 6 each have essentially the same retention factor and each be essentially the same type so that the column 10 is a balanced multicapillary column. In this invention columns are essentially the same type when they have essentially the same internal diameter, chromatographically active stationary phase and thickness of stationary phase. The multicapillary column 10 is shown having four individual capillaries but this number is not critical in the invention and any number of individual capillaries of two or more can be used.

Modern methods of production of fused silica capillary gas chromatography columns often result in a uniform product within very limited tolerances. Therefore, the columns 3, 4, 5, and 6 preferably all originate from one fused silica capillary gas chromatography column. The preferred method for making the multicapillary column 10 is to cut a single fused silica capillary gas chromatography column into four equal length sections (columns 3, 4, 5, and 6) and then to assemble these sections into the multicapillary column 10. The success of this method depends on the uniformity of the single column from which the multicapillary column 10 is made. An alternative means of terminating the bundle of individual capillaries in this event, that is believed to be feasible and that should result in a more permanent system, is to insert the end of the bundle into for example a thin walled 1/16 inch outside diameter stainless steel tube, of perhaps 2 inches in length, and then to inject an epoxy cement between the outside of the capillaries and the inside of the 1/16 inch tube. After the epoxy cement had hardened, the 1/16 inch tube could then be connected to a gas chromatograph in the conventional way with a 1/16 inch single-hole ferrule and nut.

COMPARATIVE EXAMPLE 1

A Quadrex brand (New Haven, CT) fused silica column, 822 millimeters long, 0.1 millimeter internal diameter, coated with OV-1701 of a film thickness of 0.25 micron is installed in a normally operating flame ionization detection Hewlett Packard 5790 gas chromatograph, using J&W graphite ferrules to connect the column at one end to the injector and at the other end to the detector. The graphite ferrules are one-hole ferrules having an internal diameter of 0.2 millimeter and during tightening the ferrules deform sufficiently to seal the column to the injector and to the detector. The column oven temperature is 26° C., the injection port temperature is 50° C., the detector temperature is 250° C., the carrier gas is helium at 3 psig, the make-up gas to the detector is nitrogen at 25 milliliters per minute, the hydrogen flow to the detector is 40 milliliters per minute, and the air flow to the detector is 250 milliliters per minute. A sample is prepared containing 200 parts per million (v/v) of ethyl benzene and 213 parts per million (v/v) of styrene, in air. A 2 microliter injection of the standard is made with a gas syringe. The chromatogram shows an ethyl benzene peak at about 0.4 minutes and a styrene peak at about 0.6 minutes. As expected, a larger injection volume than 2 microliters results in poorer peak efficiencies (broader peaks). The chromatogram is shown reproduced in FIG. 2.

EXAMPLE 1

A Quadrex brand fused silica column, 10 meters long, 0.1 millimeter internal diameter, coated with OV-1701 of a film thickness of 0.25 micron is repeatedly cut to produce four lengths each 822 millimeters long. The four lengths are bundled together and installed in the system of Comparative Example 1 using one-hole graphite ferrules having an internal diameter of 0.8 millimeter. The graphite ferrules deform upon tightening and seal the column bundle in the injector and the detector. The chromatographic conditions are the same as in the Comparative Example 1. An 8 microliter injection of the standard is made with a gas syringe. The chromatogram shows an ethyl benzene peak at about 0.4 minutes and a styrene peak at about 0.6 minutes. As expected, a larger injection volume than 8 microliters results in poorer peak efficiencies (broader peaks). The chromatogram is shown reproduced in FIG. 3.

Figure 2:
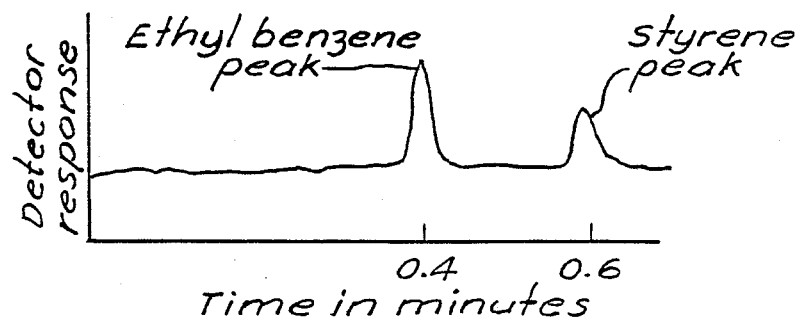
FIG. 2 is a chromatogram showing the performance of the conventional capillary column of the Comparative Example.
Figure 3:
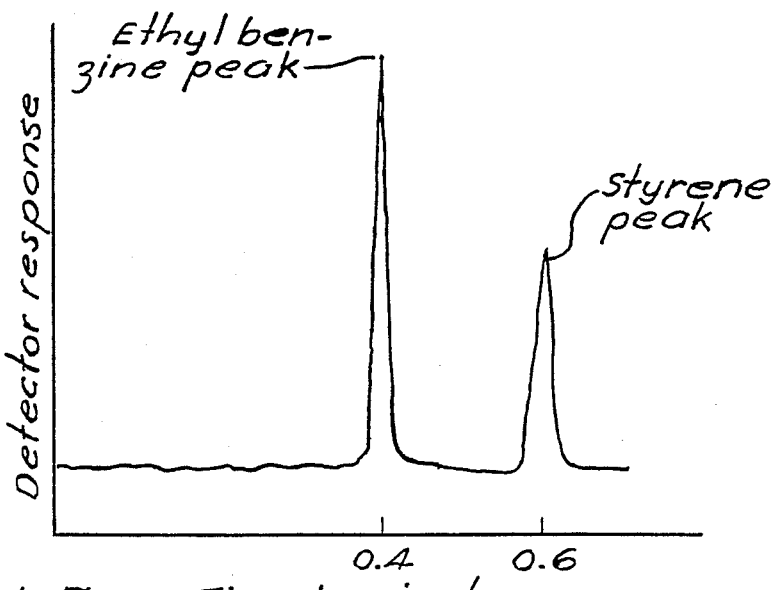
FIG. 3 is a chromatogram showing the performance of the balanced multicapillary column of Example 1.

Comparing FIG. 3 with FIG. 2 shows that the multicapillary column of Example 1 allows about a 4-fold increase in injection volume resulting in about a 4-fold increase in response without a significant reduction in resolution or efficiency and without any increase in analytical time.

What is claimed is:

1. A method of making a balanced multicapillary gas chromatography column, consisting essentially of the steps of:
   (a) cutting a single capillary gas chromatography column into a plurality of essentially equal length sections; and
   (b) assembling the sections into a bundle of the sections to make a finished column.

2. The method of claim 1 wherein the single capillary gas chromatography column is a fused silica capillary gas chromatography column.

* * * * *